United States Patent [19]

Hildebrand et al.

[11] Patent Number: 4,985,364

[45] Date of Patent: Jan. 15, 1991

[54] PREPARATION OF CYCLOPROPANECARBOXYLIC ACIDS

[75] Inventors: Heinz Hildebrand, Wuppertal; Werner Zitzmann, Leverkusen; Dieter Arlt; Heinz Kölbl, both of Cologne, all of Fed. Rep. of Germany

[73] Assignee: Bayer Aktiengesellschaft, Leverkusen, Fed. Rep. of Germany

[21] Appl. No.: 731,234

[22] Filed: May 6, 1985

[30] Foreign Application Priority Data

May 17, 1984 [DE] Fed. Rep. of Germany ....... 3418374

[51] Int. Cl.$^5$ ................. C12P 41/00; C12N 1/14; C12R 1/70; C12R 1/79
[52] U.S. Cl. .................... 435/254; 435/280; 435/919; 435/932
[58] Field of Search ............... 435/280, 253, 932, 919, 435/254

[56] References Cited

PUBLICATIONS

Pesticide Biochemistry and Physiology, Band 7, 1977, Seiten 391–401, Academic Press Inc.; D. M. Soderlund et al.: "Effects of Pyrethroid Structure on Rates of Hydrolysis and Oxidation by Mouse Liver Microsomal Enzymes" * Insgesamt *.
Chemical Abstracts, Band 104, Nr. 21, Mai 1986, Seite 514, Nr. 18488m, Columbus, Ohio, US: and JP-A-60 199 393 (Sumitomo Chemical Co., Ltd.) 10.08 1985.
T. Oritani et al., Agri. Biol. Chem. 39(1), 89–96, 1975, "Microbial Resolution of Some Racemic Monocyclic Alcohols".
S. Iriuchijima et al., Agric. Biol. Chem., 45(6), 1389–1392, (1981) "Assymetric Hydrolysis of ($\pm$)-$\beta$-- Substituted Carboxylic Acid Esters with Microorganisms".

Primary Examiner—Esther M. Kepplinger
Attorney, Agent, or Firm—Sprung Horn Kramer & Woods

[57] ABSTRACT

A process for the preparation of a ($\pm$)-trans-cyclopropanecarboxylic acid salt thereof of the formula

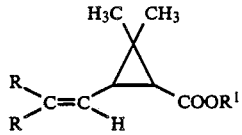

in which
R is halogen or $C_1$–$C_4$-alkyl, and
$R^1$ is hydrogen or the equivalent of a metal ion,
which comprises contacting a ($\pm$)-trans-cyclo-propanecarboxylic ester of the formula

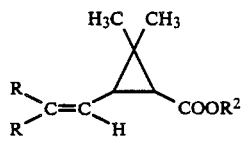

in which
$R^2$ is methyl or ethyl,
with a hydrolase which is of microbial origin and isolating the resulting ($\pm$)-trans-cyclopropanecarboxylic acid.

11 Claims, No Drawings

PREPARATION OF CYCLOPROPANECARBOXYLIC ACIDS

The present invention relates to a process for the preparation of (+)-trans-cyclopropanecarboxylic acids by the treatment of (±)-cis/(±)-trans-cyclopropanecarboxylic esters with hydrolases of microbial origin. The cyclopropanecarboxylic acids can be converted into highly effective insecticidal active compounds (pyrethroids) (see, for example, K. Naumann, Chemie derPflanzenschutzund Schädlingsbekampfungsmittel (Chemistry of Plant Protection Agents and Pesticides), edited by R. Wegler, Volume 7, published by Springer, Berlin, Heidelberg, New York, 1981), the +-trans compounds being of particular practical interest since they can be converted into particularly highly effective insecticidal pyrethroids.

It has already been disclosed, in Pesticide Biochemistry and Physiology 7, 391-401 (1977), that enzymes from mouse liver can hydrolyze certain transcyclopropanecarboxylic esters more rapidly than the corresponding cis compounds. Even if it were possible to discover and use appropriate reactions for the preparation of the particularly valuable (+)-trans-cyclopropanecarboxylic acids, the use of mammalian enzymes for industrial purposes appears unsuitable in practice.

It has now been found that (+)-trans-cyclopropanecarboxylic acids or their salts, of the general formula (I)

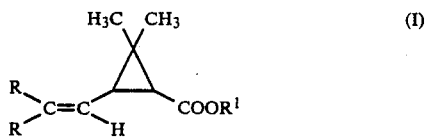

in which
R represents halogen or $C_1$–$C_4$-alkyl, and
$R^1$ represents hydrogen or the equivalent of a metal ion,
and where the steric relationships are not represented in formula (I), are obtained when the (±)-trans-cyclopropanecarboxylic esters of the general formula (II), and where appropriate mixed with the corresponding (±)-cis-cyclopropanecarboxylic esters of the general formula (II)

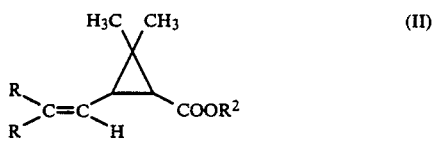

((±)-trans or mixture of (±)-trans and (±)cis) in which
R has the meaning indicated for the general formula (I), and
$R^2$ represents methyl or ethyl, where the steric relationships are not represented in formula (II),
are treated with hydrolases of microbial origin which are extracellular and/or cellular, are where appropriate and immobilized, and the resulting (+)-trans-cyclopropanecarboxylic acids or their salts of the general formula (I) are isolated and, where appropriate, purified by conventional methods, and, where appropriate, the salts are prepared.

The process according to the invention can be illustrated by the equation below (example permethric acid (ester)):

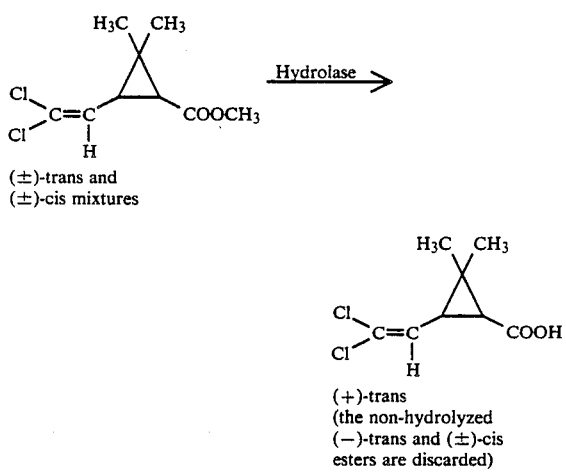

In addition, it has been found that the hydrolases (esterases) suitable for the preparation of the (+)-trans-cyclopropanecarboxylic acids and their salts of the general formula (I) are obtained when microorganisms are cultured under conventional conditions, the (±)-trans compounds (where appropriate mixed with the (±)-cis compounds) of the general formula II are treated with the product of fermentation, and the strains (or mixtures of strains) having adequate hydrolase activity are selected and the unsuitable microorganisms are discarded.

Although stereospecific reactions are frequently found in biochemistry, it was nevertheless surprising that, in the process according to the invention, the desired (+)-trans-cyclopropanecarboxylic acids can be formed stereoselectively, in a smooth manner in the mixtures of isomers, from the (±)-trans-cyclopropanecarboxylic esters of the formula II (where appropriate mixed with the (±)-cis compounds) and can be readily separated from the remaining esters.

In the general formulae (I) and (II), $C_1$–$C_4$-alkyl R denotes straight-chain or branched alkyl, such as methyl, ethyl, n- and i-propyl, and n-, iso-, sec.- and tert.-butyl. $C_1$–$C_4$-alkyl R preferably denotes methyl or ethyl, and particularly preferably methyl.

Halogen R denotes fluorine, chlorine, bromine and iodine, preferably chlorine and bromine, in particular chlorine.

Metal ions $R^1$ preferably represent alkali metal or alkaline earth metal ions, such as sodium, potassium or calcium ions.

In the general formulae (I) and (II),
R preferably represents chlorine or methyl, and
$R^1$ preferably represents hydrogen, and
$R^2$ preferably represents methyl or ethyl.

The preparation according to the invention of (+)-trans-permethric acid (general formula (I): R=Cl and $R^1$=H) from methyl (±)-trans (where appropriate mixed with (±)-cis) permethrate (general formula (II): R=Cl and $R^2$=CH$_3$) or of (+)-trans-chrysanthemic acid (general formula (I): R=CH$_3$ and $R^1$=H) from ethyl (±)-trans- (where appropriate mixed with (±)-cis) chrysanthemate (general formula (II): R=CH$_3$ and $R^2$=C$_2$H$_5$) are of particular interest.

In the "RS nomenclature", the steric relationships in the compounds of the general formulae (I) and (II) can be indicated as follows:

"(+)-trans" corresponds to "1 R trans" or "1R 3 S"

"(±)-cis" corresponds to the mixture of "1 R 3 R" and "1 S 3 S"

"(±)-trans" corresponds to the mixture of "1 R 3 S" and "1 S 3 R"

"(±)-trans and (±)-cis" mixture corresponds to "1 RS 3RS" (mixture).

In the selection of suitable microorganisms forming hydrolases (esterase), virtually all types of microorganisms are suitable, it being irrelevant whether they are procaryotic or eucaryotic microorganisms as long as they are in a position to produce the suitable hydrolases and to cleave enantioselectively compounds of the general formula (II).

Fungi of the genera Acremonium, Alternaria, Aspergillus, Fusarium, Mucor, Paecilomyces, Phoma, Stemphylium and other Zygomycota, Ascomycota, Basidiomycota or Deuteromycota, but also bacteria of the genera Arthrobacter, Bacillus, Corynebacterium, Nocardia, Pseudomonas, Rhodococcus or Streptomyces, are preferred.

The strains *Paecilomyces lilacinus* R 10 076, *Aspergillus ustus* PTB 646 A and *Pseudomonas testosteroni* ZP 50, as well as those variants and mutants of these strains which exhibit the features essential for carrying out the present invention, are very particularly preferred.

The strains R 10076, PTB 646 A and ZP 50 have been deposited at the Deutsche Sammlung von Mikro-organismen (DSM), (German collection of microorganisms), Grisebachstr. 8, 3400 Göttingen, Federal Republic of Germany:

| Short name of strain | Deposit: File number/date |
|---|---|
| R 10076 | DSM 2934/April 2, 1984 |
| PTB 646 A | DSM 2935/April 2, 1984 |
| ZP 50 | DSM 2936/April 2, 1984 |

Description of *Paecilomyces lilacinus* R 10076

The strain was isolated from a sample of soil and was given the in-house name R 10076.

On malt agar, the fungus forms colonies with a diameter of 5–7 cm within 14 days at 25° C.; the colonies are reddish violet, and the underside is colorless. The conidiophores have phiamides and are usually arranged singly, they are 400–600 μm long.

The conidia are elliptical or spindle-shaped, smooth or slightly rough, 2.5–3.0×2.0–2.2 μm.

There is no doubt that strain R 10076 is a member of the species *Paecilomyces lilacinus* (Thom) Samson 1974.

Description of *Pseudomonas testosteroni* ZP 50

Rod-shaped, Gram-negative bacteria, 0.7–0.8 μm thick and 2.1–2.9 μm long.

Motile, with polar, multitrichous flagella.

Organic growth factors are not required.

Carbohydrates, such as, for example, glucose or fructose, are not utilized. The optimal growth temperature is 30° C.

Description of *Aspergillus ustus* PTB 646 A

On malt agar, the fungus forms slow-growing colonies which are initially white or pale grey and later dark grey or black.

The conidiophores are dark-colored and up to 400 μm long; the vesicles are circular and likewise colored.

The conidia are circular, have a warty surface, and their diameter is about 4 μm.

Thus, the strain PTB 646 A is a member of the species *Aspergillus ustus* (Bain.) Thom & Church 1926.

The fermentation process according to the invention for the preparation of the preparations containing the hydrolase (esterase) can be carried out using solid, semi-solid or liquid nutrient media. Aqueous liquid nutrient media are preferably used.

The nutrient media are inoculated by generally customary methods, for example using spore suspensions, slant tubes or flask cultures.

The culturing is carried out under aerobic or anaerobic conditions, and can be carried out by the generally customary methods, such as using cultures, for example in fermentation flasks, or using air-agitated cultures or submerged cultures. The culturing is preferably carried out in an aerobic submerged process in aerated fermenters, for example in customary agitated fermentation tanks. It is possible to carry out the culture continuously or discontinuously. It is preferably carried out discontinuously.

Culturing can be carried out in all nutrient media which are known to be used for culturing microorganisms. The nutrient medium must contain one or more sources of assimilable carbon and sources of nitrogen, together with mineral salts, it being possible for these products to be present in the form of defined individual constituents as well as in the form of complex mixtures, as represented by, in particular, biological products of various origins.

Suitable sources of carbon are all customary sources of carbon. Examples which may be mentioned are carbohydrates, in particular polysaccharides, such as starches or dextrins, disaccharides, such as maltose or sucrose, monosaccharides, such as glucose or xylose, sugar alcohols, such as mannitol or glycerol, and naturally occurring mixtures, such as malt extract, molasses or whey powder. It is also possible to add hydrocarbons to the nutrient medium. Suitable sources of nitrogen are all customary organic and inorganic sources of nitrogen. Examples which may be listed are proteins, protein hydrolysates, aminoacids, such as glutamic acid, aspartic acid, meat meal, meat hydrolysates, and soya bean meal, cottonseed meal, lentil meal, pea meal, soluble and insoluble plant proteins, corn steep liquor, yeast extract, peptones and meat extract, as well as ammonium salts and nitrates, for example $NH_4Cl$, $(NH_4)_2SO_4$, urea, $NaNO_3$ and $KNO_3$. The mineral salts which the nutrient medium should contain provide the following ions, for example:

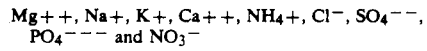

$Mg^{++}$, $Na^+$, $K^+$, $Ca^{++}$, $NH_4^+$, $Cl^-$, $SO_4^{--}$, $PO_4^{---}$ and $NO_3^-$ as well as ions of the customary trace elements, such as Cu, Fe, Mn, Mo, Zn, Co and Ni. If the sources of carbon or nitrogen or the water used do not contain sufficient amounts of these salts or trace elements, it is advantageous to supplement the nutrient medium accordingly. The composition of the nutrient media can be varied within wide limits. The type and composition of the nutrient medium will generally depend on those constituents which are available especially favorably in particular cases. In general, the nutrient solutions preferably contain about 0.5 to 8%, in particular 0.6 to 6%, of sources of carbon, preferably about 0.5 to 4%, in particular 0.5 to 3%, of sources of nitrogen, and preferably about 0.001 to 0.5%, in particular 0.003 to 0.3%, of mineral salts.

Over and above the constituents of the suture solutions necessary for the growth of the microorganisms, it is possible to add to the media other additives which can lead to an increase in the rate of enzyme formation by the microorganisms or to an increase in the overall volumetric yield of enzyme. In addition, substances of this type can lead to an improvement in the isolation of the enzyme or facilitate its liberation, or can serve to stabilize the cells when whole cells are used in the free or immobilized state for the reaction.

The abovementioned additives to the nutrient media can be emulsifiers and surface-active substances, such as, for example, Tween 80, Brij 58, benzyl alcohol, phenethyl alcohol, Triton X 100, as well as aliphatic alcohols of various chain-lengths, and hydrocarbons.

The pH of the growing cultures should preferably be maintained between about 5 and about 10, in particular between 6.5 and 9.5. Too great a decrease of the pH into the acid range can be prevented by the addition of an organic or inorganic base, preferably $CaCO_3$. As customary in fermentation technology, it is also possible to carry out automatic pH control, in which sterile organic or inorganic acid, for example $H_2SO_4$, or sterile alkali, for example NaOH, is injected into the culture solution at intervals.

It is advantageous to ensure that the microorganisms are brought into adequate contact with oxygen (for microorganisms cultured aerobically) and with the nutrients. This can be carried out by the generally customary methods, such as shaking and stirring.

The culture temperature can be between about 15° and about 80° C., preferably between 20° or 25° C. and 35° or 40° C., and it is particularly preferably about 26° C. The culture time can be varied widely, the composition of the nutrient medium and the culture temperature, for example, being of importance. The optimal conditions in each case can readily be determined by all skilled in the area of microbiology.

It has emerged that the amount of the compound according to the invention which accumulates in the culture broth generally reaches its maximum about 1 to 10, preferably about 3 to 5, days after starting the culture. The desired esterase activity of the fermentation can be quantitatively measured using spectrophotometric, liquid chromatographic and gas chromatographic methods.

As is general with microbiological processes, foreign infections of the culture media should be prevented. The customary measures are applied for this, such as sterilization of the nutrient media, of the culture vessels and of the air necessary for aeration. It is possible to use, for example, both steam and dry sterilization to sterilize the equipment, it being possible for the temperatures to be, preferably, 100° to 140° C., in particular 120° to 130° C.

If foam is produced in an undesired amount during culture, it is possible to add the customary chemical foam suppressants, for example liquid fats and oils, oil-/water emulsions, paraffins, higher alcohols, such as octadecanol, silicone oils, polyoxyethylene or polyoxypropylene compounds (for example in amounts up to about 1%). Foam can also be suppressed or eliminated using customary mechanical equipment (which uses, for example, centrifugal forces).

As already indicated above, the microorganisms suitable for the preparation of the (+)-trans compounds can readily be selected by a simple screening process. Available microorganism strains are used for this purpose in a customary manner, for example in a culture flask. The cells are removed from the product of fermentation. Substrate (for example 1 ml of an emulsion of 2.23 mg of methyl (±)-t-rans-permethrate in 1 ml of 0.1 M phosphate buffer) is added to a small portion (for example 1 ml) of the fermentation broth, and the mixture is shaken at about 30° C. and pH 7 for about 15 hours. The reaction is stopped by addition of acid (for example 0.1 ml of 5 N HCl), and the aqueous reaction mixture is extracted with ethyl acetate, and the content of desired product is determined by high-pressure liquid chromatography (HPLC). It is possible in this manner to establish the presence of extracellular hydrolase. For the determination of a cell-bound hydrolase, the substrate is added correspondingly to an aqueous suspension of the cells (for example mycelium) which have been separated off and washed. By using this straightforward method, it is possible to select suitable microorganisms, to undertake optimization in respect of the substrate used, as well as to determine whether the hydrolase is extracellular and/or cell-bound.

The process for working up the product of fermentation and of the hydrolyse of the (±)-trans (where appropriate mixed with (±)-cis) compounds of the general formula (II), followed by separation off, is advantageously carried out as follows, there resulting different process measures when the hydrolase (esterase) is cell-free or cell-bound, or both cell-free and cell-bound.

In order to obtain the preparation of an extra-cellular hydrolase, after fermentation is complete the fermentation broth is separated from the cells by the customary methods (for example by centrifugation). The enzyme (together with other protein constituents) is precipitated out of the resulting cell-free fermentation broth likewise by customary methods (for example addition of alcohols, such as methanol or ethanol, or of inorganic salts, such as ammonium sulphate). The precipitate is separated off (for example by centrifugation) and dissolved in a buffer solution (for example phosphate buffer). This solution can be used directly for carrying out the hydrolysis step. In the case where the enzyme is cell-bound, the cells which have been separated off can be suspended in a buffer solution and used directly for the hydrolysis. It is not normally necessary to undertake further purification of these enzyme preparations. However, further working up of the enzyme preparations can readily be carried out by the generally customary methods (for example reprecipitation methods, chromatographic methods, liberation of cell-bound enzyme by cell fragmentation, etc.) and this is particularly desirable when the enzyme is to be used, by the customary methods, in a modified form, for example bound to solid inorganic or organic carriers (for example zeolites, polysaccharides, polyamides, polystyrene resins, polyacrylic resins etc.) or microencapsulated (immobilized enzyme).

The conversion of the (±)-trans compounds (where appropriate mixed with the (±)-cis isomers) of the general formula (II) (in the following text abbreviated to "cyclopropanecarboxylic esters") into the (+)-trans compounds of the general formula (I) (in the following text abbreviated to "cyclopropanecarboxylic acids") using the above enzyme preparations is advantageously carried out as follows:

In the case where the enzyme is extracellular, that is to say in aqueous solution, the enzyme preparation is added to an emulsion or a suspension of the cyclopropanecarboxylic ester in an aqueous buffer solution and the mixture is stirred. The hydrolysis reaction is followed by high-pressure liquid chromatographic or gas chromatographic investigations of samples taken from time to time. The pH range can vary over wide ranges depending on the substrate and enzyme. The process is preferably carried out between pH 5 and pH 10, particularly preferably between pH 6 and 9, and very particularly preferably between pH 6.5 and 8.8. The pH values can readily be adjusted or maintained by using suitable buffer systems (for example phosphate buffer or tris buffer). The reaction temperatures are between 15° and 80° C., preferably between 20° and 40° C., and particularly preferably between 25° and 35° C.

To stop the reaction, the pH is made very acid (for example pH 1 to 2, preferably 1.2 to 1.8) by addition of acid (for example $H_2SO_4$ or HCl). The reaction mixture is then extracted with organic solvents which are sparingly miscible with water, such as, where appropriate, halogenated aliphatic or aromatic hydrocarbons, for example methylene chloride, esters, for example ethyl acetate, or ethers, for example diethyl ether, or their mixtures. The organic phase (also designated "organic phase I" in the following text) is separated off for further work-up, and the aqueous phase is discarded.

In the case where the hydrolase is cell-bound, the process is carried out correspondingly. The only deviation from the above procedure is that a suspension of the cells (or of the mycelium) in water is used in place of the aqueous solution of the hydrolase, the reaction mixture is shaken until the reaction is terminated, and the cells are then separated off (for example by centrifugation). The "organic phase I" is obtained from the aqueous reaction mixture as described above.

For further work-up, an aqueous alkali solution (for example of sodium or potassium hydroxide, sodium or potassium bicarbonate or sodium or potassium carbonate), which has a pH between 8 and 10, is added to the "organic phase I". The mixture is shaken to extract, the aqueous phase is separated off, and the remaining organic phase (where appropriate after repetition of the extraction) is discarded Then the resulting aqueous solution is acidified (for example to pH 1 to 3 using 5N HCl), and an organic solvent which is sparingly miscible with water is added, it being possible to use the same solvents as listed above for the preparation of the "organic phase I". The mixture is shaken to extract, and the organic phase (organic phase II) is separated off for further work-up, and the aqueous phase is discarded. The optical purity of the resulting cyclopropanecarboxylic acids can be determined by measuring the rotation, and they can be isolated in a customary manner by distilling off the solvent. If desired, the salts of the cyclopropanecarboxylic acids can be obtained by reaction with bases (for example alkali metal or alkaline earth metal hydroxides or carbonates).

The process according to the invention can also be carried out using the modified (for example immobilized) enzymes in a corresponding manner using the customary methods.

The biochemical procedures and methods which can be used within the framework of the process according to the invention are described in Bryan Williams and Keith Wilson, Principles and Techniques of Practical Biochemistry, Edward Arnold (Publishers) Ltd., London, 1975 and the corresponding German edition, Practical Biochemistry, published by Georg Thieme, Stuttgart, 1978, where there are also many references to further literature.

Materials and trademarks used:
Tween 80 is a polyoxyethylene-sorbitan.
Tween is a trademark of ICI America Inc., Atlas Chemicals Division, U.S.A.
Brij 58 is a polyoxyethylene monocetyl ether.
Brij is a trademark of ICI America Inc., Atlas Chemicals Division, U.S.A.
Triton X-100 is a p-t-octylphenyl polyethylene glycol ether.
Triton is a trademark of Rohm & Haas, U.S.A.
Baylith T 144 is a zeolite.
Baylith is a trademark of Bayer AG, Leverkusen, Federal Republic of Germany.
Bacto Peptone is a protein hydrolysate of Difco Laboratories, Detroit, U.S.A.

The process according to the invention is intended to be illustrated by the examples which follow (all percentage data relate to % by weight unless otherwise indicated):

EXAMPLE 1

Screening method

The fermentation of the microorganisms to be tested is carried out in 1 liter flasks in a customary manner. After the cells have settled, 1 ml of an emulsion of 2.23 mg of methyl ($\pm$)-trans-permethrate (compound of formula (II) with R=Cl and $R^2=CH_3$) in 0.1 molar phosphate buffer is added to 1 ml of the fermentation broth, and the mixture (pH 7) is shaken at 30° C. for 12 hours. Then 0.1 ml of 5N HCl is added, and the mixture is extracted with 2 ml of ethyl acetate. The organic phase is examined by HPLC analysis (reversed phase chromatography) on a RP 10 column (supplied by Merck, Darmstadt, Federal Republic of Germany) with a UV detector, and thus is established whether and to what extent the particular strain produces hydrolases which convert the starting material into (+)-trans-permethric acid (compound of the formula (I) with R=Cl and $R^1=H$). In a corresponding manner, to find cell-bound hydrolases 1 ml of an aqueous cell suspension is used in place of the culture broth.

EXAMPLE 2

Hydrolase from *Paecilomyces lilacinus* R 10076

100 ml of a culture medium which contains 3% soy meal, 2% glucose and 0.5% $K_2HPO_4$ is sterilized by heating to the boiling point in a 1,000 ml conical flask.

After the sterilization, the pH of the medium is adjusted to pH 7.0 using sterile 1 M hydrochloric acid and sterile 1 M sodium hydroxide solution.

The medium is inoculated using an inoculation loop from a slant tube culture of the strain *Paecilomyces Lilacinus* R 10076.

Culturin lasts 120 hours until a hih enzymatic activity is reached, and is carried out at 26° C. in a shaking machine. The mycelium is removed from the culture broth by centrifugation; 70 ml of methyl ($\pm$)-transpermethrate emulsion (2.23 mg/ml of rethyl ($\pm$)-transpermethrate in 0.1 M phosphate buffer, pH 8.0) are added to the latter. The reaction is incubated at 30° C., with shaking, for 20 hours. It is then acidified to pH 1.5 by addition of 5 H HCl, and extracted with 100 ml of $CH_2Cl_2$ (organic phase I). The "organic phase I" is then shaken with 100 ml of 0.1N $Na_2CO_3$. The aqueous $Na_2CO_3$ phase is then adjusted to pH 1.5 with 5N HCl, and is extracted with 100 ml of CH$_2$Cl$_2$ ("organic phase II"). The "organic phase II" is dried with Na$_2$SO$_4$; its content of (+)-trans-permethric acid is determined by liquid chromatography, and its rotation is measured. Content of (+)-trans-permethric acid: 31.2 mg; $\alpha_D^{20}$ = +0.048; optical purity 70%.

EXAMPLE 3

Hydrolase from *Aspergillus ustus* PTB 646 A 100 ml of a culture medium which contains 2% of yeast extract, 2% of glycerol and 0.25% of CaCO$_3$ is sterilized by heating to boiling in a 1,000 ml conical flask.

After sterilization, the pH of the medium is adjusted to pH 7.0 using sterile 1 M hydrochloric acid and sterile 1 M sodium hydroxide solution.

The medium is inoculated using an inoculation loop from a slant tube culture of the strain *Aspergillus ustus* PTB 646 A.

Culture lasts 72 hours until a high enzymatic activity is reached, and is carried out at 26° C. in a shaking machine. 70% of the enzyme is then located inside the cells.

The cells are removed by centrifugation (10 g wet mass), and are mixed with 70 ml of buffer (0.1 mol/tris, pH 9.2) and 200 g of glass beads (size 0.075–0.150 mm).

The cells are fragmented in a "Vibrogen-Zellmühle Vi 4" (supplied by Buühler, Tübingen), with water cooling (15 min), and then the suspension is centrifuged until clear. 10 ml of a suspension of methyl (±)-trans-permethrate (10 mmol/l) in tris buffer (0.1 mol/l, pH 8.2) are added to 10.0 ml of the supernatant, and the mixture is incubated at 30° C. The reaction is stopped after 16 h by addition of 2 ml of 12N H$_2$SO$_4$, and is extracted with 1 part by volume of ethyl acetate.

The oranic phase is analyzed by HPLC; 13.77 μmol of trans-permethric acid (13.8% conversion) are found. The acid is isolated by fractional extraction. For this purpose, the ethyl acetate phase is extracted with 0.1 M Na$_2$CO$_3$. The organic phase which has been separated off is discarded. The aqueous phase is acidified to pH 2 with dilute H$_2$SO$_4$ and then extracted with ethyl acetate. The ethyl acetate phase is separated off, and the solvent is distilled off. The desired acid remains as the residue. It has a rotation of $[\alpha]_D$ = +0.140 (c=0.46, EtOH). The optical purity is 82%.

EXAMPLE 4

Hydrolase from *Pseudomonas testosteroni* ZP 50

100 ml of a culture medium which contains 3% Bacto Peptone, 1.5% yeast extract and 0.5% K$_2$HPO$_4$ is sterilized by heating to boiling in a 1,000 ml conical flask.

The sterilized medium is inoculated using an inoculation loop from a slant tube culture of the strain *Pseudomonas testosteroni* ZP 50.

The culture lasts 36 hours until a high enzymatic activity is reached, and is carried out at 26° C. in a shaking machine. The enzyme is predominantly located inside the cells.

The cells are removed by centrifugation (10 g moist weight) and suspended in 70 ml of 0.1 M phosphate buffer, pH 8.5, and mixed with 200 g of lass beads (0.075–0.150 mm diameter). The cells are destroyed by shaking in a cell mill (15 min) ("Vibrogen" type, supplied by Bachofen), and the cell debris is removed by centrifugation.

The supernatant is tested for methyl trans-permethrate esterase activity. For this purpose, a suspension of methyl (±)-trans-permethrate (10 mmol/l) in phosphate buffer (0.1 mol/l, pH 8.5) is prepared, and 1.0 ml of the crude cell liquor is mixed with 1.0 ml of the ester suspension. Incubation is carried out at 35° C. for 1 h, then the reaction is stopped with 100 μl of 12N H$_2$SO$_4$, and the mixture is extracted with 2.0 ml of ethyl acetate. The organic phase is analyzed for the content of methyl (±)-trans-permethrate and permethric acid by HPLC.

Result: 1 ml of the crude cell liquor hydrolyzes 0.01 μmol of methyl (±)-trans-permethrate in one minute.

The content of (+)-enantiomers in the acid is determined by gas chromatography. It is 99% (+)-enantiomer.

EXAMPLE 5

Immobilization of the esterase 10 g of cells of *Pseudomonas testosteroni* ZP 50 are suspended in 70 ml of phosphate buffer (0.1 mol/l, pH 8.5) and disrupted with 200 g of glass beads in a cell mill ("Vibrogen" type). The mixture is centrifuged, and ammonium sulphate (up to 40% of the saturation concentration) is added to the supernatant. The resulting precipitate is discarded. Further ammonium sulphate, up to 60% of the saturation concentration, is added to the resulting supernatant.

The resulting precipitate, which contains the enzyme, is removed by centrifugation and dissolved in 10 ml of phosphate buffer (0.1 mol/l, pH 7.0). The solution is dialyzed against 10 l of phosphate buffer (0.1 mol/l, pH 7.0) overnight.

10.0 g of type "Baylith T 144" zeolite are silanized by a standard method (H. H. Weetall: "Covalent Coupling Methods for Inorganic Support Materials" in: S. P. Colowick, N. O. Kaplan (eds.): Methods in Enzymology, Vol. XLIV, p. 140). For this purpose, 40 ml of 3-aminopropyltriethoxysilane (10% strength solution in water) (supplied by Ega-Chemie, Federal Republic of Germany) are added to the zeolite, the pH is adjusted to 3.5 by 6N HCl, and the mixture is incubated at 75° C. for 20 min in a shaking waterbath. The solid is then filtered off with suction, washed with water and dried at 115° C. for 5 h.

250 ml of glutardialdehyde (2.5% strength solution in phosphate buffer, 0.05 mol/l, pH 7.0) are now added to the zeolite, and the mixture is shaken for 90 min. The solid is then filtered off, washed with water, and the dialyzed enzyme solution is added (10 ml). The mixture is shaken for 4 h, and the solid is filtered off with suction and washed with phosphate buffer (0.1 mol/l, pH 7.0).

The immobilized and the free enzyme are assayed by mixing, on the one hand, 1.0 g of enzyme-loaded zeolite with 1.0 ml of phosphate buffer (see above) and, on the other hand, 1.0 ml of the dialyzed enzyme solution with 1.0 ml of methyl (±)-trans-permethrate suspension, and incubating at 35° C. for 1 h. The assays are stopped with 12N H$_2$SO$_4$, extracted with 2.0 ml of ethyl acetate, and analyzed by HPLC.

Result:

| Activity of the free enzyme | 0.11 | $\frac{\mu mol}{(min \times ml)}$ |
|---|---|---|
| Activity of the immobilized enzyme | 0.012 | $\frac{\mu mol}{(min \times g)}$ |

Yield of active enzyme 10.9%.

EXAMPLE 6

Hydrolysis of ethyl (+)-chrysanthemate with *Pseudomonas testosteroni* ZP 50

1.5 g of cells (wet weight) of *Pseudomonas testosteroni* ZP 50 are suspended in 3.0 ml of phosphate buffer (0.1 mol/l, pH 8.5). 6.0 mg of ethyl (±)-cis, transchrysanthemate (R=CH₃ and R²=C₂H₅) are emulsified in 3.0 ml of phosphate buffer (0.1 mol/l, pH 8.5) with the addition of Brij 58 g (80 mg/l). The solutions are mixed and incubated, with shaking, at 30° C. for 16 h.

Then 300 μl of 12N sulphuric acid are added, as well as 6.0 ml of ethyl acetate for extraction.

The ethyl acetate phase is separated off and analyzed by high-pressure liquid chromatography. 0.16 mg/ml of (±)-trans-chrysanthemic acid (R=CH₃ and R¹=H) is found. The ethyl acetate solution is also extracted with 1 volume of sodium carbonate solution (0.1 mol/l). After phase separation, the aqueous phase is adjusted to pH 1.5 and extracted with 1 volume of chloroform. The phases are separated, the organic phase is adjusted to 1.5 ml, and the optical rotation is measured in a polarimeter. $\alpha = +0.07$ (c=0.06).

It will be understood that the specification and examples are illustrative but not limitative of the present invention and that other embodiments within the spirit and scope of the invention will suggest themselves to those skilled in the art.

We claim:

1. A process for the preparation of a (+)-trans-cyclopropanecarboxylic acid salt of the formula

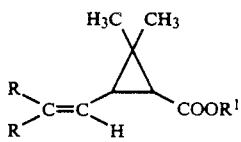

in which

R is halogen or $C_1$-$C_4$-alkyl, and $R^1$ is hydrogen or one equivalent of a metal ion, which comprises contacting a (±)-trans-cyclopropanecarboxylic ester of the formula

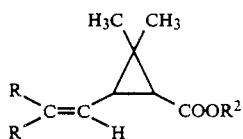

in which $R^2$ is methyl or ethyl, with an esterase which is of microbial origin for a time and under conditions to effect hydrolysis, and isolating the resulting (+)-trans-cyclopropanecarboxylic acid.

2. The process according to claim 1, in which R is chlorine or methyl.

3. The process according to claim 1, wherein the ester comprises methyl (±)-trans permethrate and the product comprises (+)-trans-permethric acid.

4. The process according to claim 1, wherein the ester comprises ethyl (±)-trans chrysanthemate and the product comprises (+)-trans-chrysanthemic acid.

5. The process according to claim 1, wherein the contact is carried out at a pH between 6 and 9.

6. The process according to claim 1, wherein the contact is carried out at a temperature between 25° and 80° C.

7. The process according to claim 1, wherein the esterase is in an immobilized form.

8. The process according to claim 1, wherein the (±)-trans ester is mixed with the corresponding (±)-cis ester.

9. The process according to claim 1, wherein the esterase is cell-bound during the contact.

10. The process according to claim 1, wherein the esterase is produced by the micro-organism strain *Paecilomyces lilacinus* (DSM 2934), *Aspergillus ustus* (DSM 2935) or *Pseudomonas testosteroni* (DSM 2936).

11. A biologically pure culture of microorganism *Paecilomyces lilacinus* (DSM 2934) or *Aspergillus ustus* (DSM 2935).

* * * * *